United States Patent
Heckroth et al.

(10) Patent No.: US 9,468,701 B2
(45) Date of Patent: *Oct. 18, 2016

(54) ISOCYANATE-FUNCTIONAL PREPOLYMER FOR A BIOLOGICALLY DEGRADABLE FABRIC ADHESIVE

(71) Applicant: Adhesys Medical GmbH, Aachen (DE)

(72) Inventors: Heike Heckroth, Odenthal (DE); Christoph Eggert, Köln (DE); Jörg Hofmann, Krefeld (DE); Klaus Lorenz, Dormagen (DE)

(73) Assignee: Adhesys Medical GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,711

(22) Filed: May 16, 2016

(65) Prior Publication Data

US 2016/0256595 A1    Sep. 8, 2016

Related U.S. Application Data

(62) Division of application No. 14/365,295, filed as application No. PCT/EP2012/075823 on Dec. 17, 2012, now Pat. No. 9,375,509.

(30) Foreign Application Priority Data

Dec. 20, 2011   (EP) ..................................... 11194416

(51) Int. Cl.

| A61L 24/04 | (2006.01) |
|---|---|
| A61L 24/00 | (2006.01) |
| C08G 18/48 | (2006.01) |
| A61L 24/06 | (2006.01) |
| C08G 65/333 | (2006.01) |
| C08G 18/10 | (2006.01) |
| C08L 71/02 | (2006.01) |
| C08G 18/73 | (2006.01) |
| C08G 65/26 | (2006.01) |
| C08G 65/332 | (2006.01) |

(52) U.S. Cl.
CPC .......... *A61L 24/046* (2013.01); *A61L 24/0042* (2013.01); *A61L 24/06* (2013.01); *C08G 18/10* (2013.01); *C08G 18/4837* (2013.01); *C08G 18/4866* (2013.01); *C08G 18/4887* (2013.01); *C08G 18/73* (2013.01); *C08G 65/2663* (2013.01); *C08G 65/332* (2013.01); *C08G 65/3322* (2013.01); *C08G 65/33348* (2013.01); *C08L 71/02* (2013.01); *C08L 2205/05* (2013.01)

(58) Field of Classification Search
None
See application file for complete search history.

(56) References Cited

U.S. PATENT DOCUMENTS

| 3,404,109 A | 10/1968 | Milgrom |
|---|---|---|
| 3,829,505 A | 8/1974 | Herold |
| 3,941,849 A | 3/1976 | Herold |
| 4,355,188 A | 10/1982 | Herold et al. |
| 4,721,818 A | 1/1988 | Harper et al. |
| 4,877,906 A | 10/1989 | Harper |
| 4,987,271 A | 1/1991 | Watabe et al. |
| 5,032,671 A | 7/1991 | Harper |
| 5,099,075 A | 3/1992 | Katz et al. |
| 5,158,922 A | 10/1992 | Hinney et al. |
| 5,391,722 A | 2/1995 | Chandalia et al. |
| 5,470,813 A | 11/1995 | Le-Khac |
| 6,780,813 B1 | 8/2004 | Hofmann et al. |
| 7,008,900 B1 | 3/2006 | Hofmann et al. |
| 2004/0068078 A1 | 4/2004 | Milbocker |
| 2005/0027145 A1 | 2/2005 | Hofmann et al. |
| 2009/0012206 A1 | 1/2009 | Heckroth et al. |
| 2009/0191145 A1 | 7/2009 | Heckroth et al. |
| 2009/0221071 A1 | 9/2009 | Heckroth et al. |
| 2011/0123479 A1 | 5/2011 | Heckroth et al. |
| 2012/0244107 A1 | 9/2012 | Heckroth et al. |
| 2012/0276382 A1 | 11/2012 | Dorr et al. |
| 2013/0123532 A1 | 5/2013 | Gurtler et al. |
| 2013/0325062 A1 | 12/2013 | Heckroth et al. |

FOREIGN PATENT DOCUMENTS

| CA | 2780919 A1 | 4/2011 | |
|---|---|---|---|
| DE | 3132258 A1 | 6/1982 | |
| DE | WO 2011047789 A1 * | 4/2011 | ............ A61L 31/06 |
| EP | 385619 A2 | 9/1990 | |
| EP | 406440 A1 | 1/1991 | |

(Continued)

*Primary Examiner* — Randy Gulakowski
*Assistant Examiner* — Christopher M Rodd
(74) *Attorney, Agent, or Firm* — Drinker Biddle & Reath LLP

(57) ABSTRACT

The present invention relates to an isocyanate functional prepolymer that can be achieved through
   a) a reaction of an H functional starter compound having at least one Zerewitinoff active H atom with an alkylene oxide and a comonomer to a preliminary stage bearing hydroxyl groups, wherein said comonomer is selected from the group comprising lactides, glycolides, cyclical dicarboxylic acid anhydrides as well as combinations thereof and wherein said comonomer is integrated through statistical copolymerization into the polymer chain(s) of the preliminary stage bearing hydroxyl groups, and
   b) a reaction of the preliminary stage bearing hydroxyl groups from step a) with a polyfunctional isocyanate to an isocyanate functional prepolymer.

The invention additionally relates to a process for producing this isocyanate functional prepolymer, a tissue adhesive system containing such an isocyanate functional prepolymer and a dispensing system having at least two chambers and this type of tissue adhesive system.

14 Claims, No Drawings

(56) References Cited

FOREIGN PATENT DOCUMENTS

| | | |
|---|---|---|
| EP | 0700949 A2 | 3/1996 |
| EP | 0743093 A1 | 11/1996 |
| EP | 0761708 A2 | 3/1997 |
| EP | 1525244 A1 | 4/2005 |
| EP | 1752481 A1 | 2/2007 |
| EP | 2011808 A1 | 1/2009 |
| EP | 2046861 A1 | 4/2009 |
| EP | 2145634 A1 | 1/2010 |
| EP | 2336212 A1 | 6/2011 |
| EP | 10163170 | 11/2011 |
| EP | 11153810 | 8/2012 |
| JP | 4145123 B2 | 9/2008 |
| WO | WO-97/40086 A1 | 10/1997 |
| WO | WO-98/16310 A1 | 4/1998 |
| WO | WO-00/47649 A1 | 8/2000 |
| WO | WO-01/39883 A1 | 6/2001 |
| WO | WO-01/80994 A1 | 11/2001 |
| WO | WO-2006/010278 A1 | 2/2006 |
| WO | WO-2009106245 A2 | 9/2009 |
| WO | WO-2011047789 A1 | 4/2011 |
| WO | WO-2011069973 A2 | 6/2011 |

* cited by examiner

ISOCYANATE-FUNCTIONAL PREPOLYMER FOR A BIOLOGICALLY DEGRADABLE FABRIC ADHESIVE

CROSS-REFERENCE TO RELATED APPLICATIONS

This application is a divisional application of U.S. patent application Ser. No. 14/365,295, filed Jun. 13, 2014, which is a national stage application (under 35 U.S.C. §371) of PCT/EP2012/075823, filed Dec. 17, 2012, which claims benefit of European Application No. 11194416.1, filed Dec. 20, 2011, both of which are incorporated herein by reference in their entirety.

The present invention relates to an isocyanate functional prepolymer as well as to a process for the production thereof. The invention also relates to a tissue adhesive system containing such an isocyanate functional prepolymer, and a dispensing system having at least two chambers and this type of tissue adhesive system.

In the recent past, growing interest has developed for replacing or assisting surgical sutures through the use of suitable adhesives. Particularly in the field of plastic surgery, where emphasis is placed on thin, mostly unnoticeable scars, adhesives are being used more frequently.

To be accepted as a suture replacement for surgeries, tissue adhesives have to have a variety of special properties. This includes an ease of use and an adequate viscosity so that the adhesive cannot penetrate or run into deeper layers of tissue. In classical surgery, rapid hardening is additionally required, whereas in plastic surgery, correcting the adhesive joint should be possible and therefore the hardening speed may not be too high. The adhesive also has to be biocompatible and may not have histotoxicity or thrombogenicity or an allergenic potential.

Various materials used as tissue adhesives are commercially available. This includes the cyanoacrylates, Dermabond® (octyl-2-cyanoacrylate) and Histoacryl Blue® (butyl cyanoacrylate). However, a rapid hardening time and brittleness of the bonded area limit its use. Cyanoacrylates are only suitable for external use due to their poor biodegradability.

Biological adhesives, such as BioGlue®, a mixture of glutaraldehyde and bovine serum albumin, various collagens and gelatin-based systems (FloSeal®) as well as fibrin adhesive (Tissucol), are available as an alternative to cyanoacrylates. The primary role of these systems is to stop bleeding (hemostasis). In addition to high costs, fibrin adhesives feature a relatively weak adhesive strength and rapid breakdown, such that they can only be used for less severe injuries on tissue that is not stretched. Collagen and gelatin-based systems, such as FloSeal® work exclusively to attain hemostasis. Additionally, there is always a risk of infection with biological systems as fibrin and thrombin are extracted from human material and collagen and gelatin from animal material. Furthermore, biological materials must be stored in refrigeration, therefore they cannot be used for emergency care, such as in disaster areas, for military exercises, etc. In this case, trauma injuries can be treated with QuikClot® or QuikClot ACS+™, which are a mineral granulate that is applied to the wound in an emergency and causes coagulation by withdrawing water. QuikClot® produces a highly exothermic reaction, which leads to burns. QuikClot ACS+™ is gauze, into which salt is embedded. The system must be firmly pressed against the wound to stop bleeding.

EP 2 011 808 A1 refers to tissue adhesives that are based on a hydrophilic 2-component polyurethane system. These tissue adhesives can be used to cover, close or bond cell tissue, and particularly to bond wounds. The described tissue adhesives are distinguished by a strong bond to the tissue, a high level of flexibility of the achieved joining seam, ease of application, a broadly adjustable hardening time, and high bio-compatibility.

However, certain problems also arise when using conventional tissue adhesive. Thus, a swelling of the tissue adhesive may occur due to hydrophily of the polyurethane system when exposed to water for longer periods. As a result, the bond of the tissue adhesive to the tissue is reduced, which can have an overall negative impact on the durability of the bond.

EP 2 145 634 A1 highlights 2K adhesive systems based on polyurea. These can be achieved through a reaction of isocyanate functional prepolymers based on aliphatic isocyanates having secondary diamines especially and structurally derived from amino acids. These adhesive systems are particularly suitable as hemostatic agents for stopping bleeding and also have beneficial bonding properties. Furthermore, these systems allow tissue pieces to be rejoined or bonded together even in the case of more severe injuries, which is beneficial for the healing process of wounds.

The polyurea-based adhesive revealed in EP 2 145 634 A1, however, is primarily designed for external application. Thus, for an application in the body, it is necessary that the adhesive degrades there after the wound has healed. This is not the case with convention adhesive.

WO 2009/106245 A2 highlights the production and use of polyurea systems as tissue adhesive. The systems revealed therein comprise at least two components. This involves an amino-functional aspartic acid ester and an isocyanate-functional prepolymer, which can be attained through the reaction of aliphatic polyisocyanates with polyester polyols. The two-component polyurea systems described can be used as tissue adhesive for closing wounds in human and animal cell structures. In doing so, a very positive adhesive result can be achieved. Polyurea systems have been designed in such a way that they biologically degrade within a period of up to 6 months.

In the case of systems revealed in WO 2009/106245 A2, the ester group primarily divided during biological degradation is found in the polyol component of the prepolymer used. The production of a respective component is tied to a relatively large effort.

Thus, it is desirable to provide a new prepolymer that is not only easier to access but also has an additional or alternative functional group that can be split under physiological conditions. Therefore, the goal of the invention was to provide a prepolymer that is easily accessible, has good degradability under physiological conditions, and quickly transforms to a material with positive adhesive qualities with a hardener under physiological conditions.

This task was solved by an isocyanate functional prepolymer, which is available through a) a reaction of an H functional starter compound having at least one Zerewitinoff active H atom with an alkylene oxide and a comonomer to a preliminary stage bearing hydroxyl groups, wherein said comonomer is selected from the group comprising lactides, glycolides, cyclical dicarboxylic acid anhydrides as well as combinations thereof and wherein said comonomer is integrated through statistical copolymerization into the polymer chain(s) of a preliminary stage bearing hydroxyl groups, and b) a reaction of the preliminary stage bearing hydroxyl groups from step a) with a polyfunctional isocyanate to an isocyanate functional prepolymer.

In other words, the isocyanate functional prepolymer in the polymer chains pursuant to the invention contains ester groups that are produced through statistic copolymerization of alkylene oxide compounds and lactides, glycolides and/or cyclical dicarboxylic acid anhydrides on starter compounds containing Zerewitinoff active H atoms. The ester groups in particular are not integrated in blocks. In the process, the indefinite article "a", "an", etc. means that respectively even several of these components can be optionally reacted with each other. The specified components, particularly the comonomer, can also be used dimeric and trimeric, for example as a dilactide.

Surprisingly, it was demonstrated that such isocyanate functional prepolymers are biologically degradable, for example, in the body of a patient. In this regard, the degradation period beyond the duration of healing of the closing wound is, for example, 4 weeks. In this context, particularly the statistic distribution of comonomer units in the polymer chain(s) seems to work beneficially on the speed of degradation, as they function as "predetermined breaking points" in the hardened adhesive. If the comonomer components are affected or broken up during the biological degradation, the polymer chain length shortens very rapidly as a result.

Simultaneously, the isocyanate functional prepolymers pursuant to the invention are distinguished by a high adhesion, particularly to human or animal tissue as well as a high hardening speed. Moreover, the adhesive systems having an isocyanate functional prepolymer pursuant to the invention meet the requirements with regard to the aforementioned histotoxicity, thrombogenicity, and allergenic potential.

The scope of the present invention provides that the H functional starter compound bears at least one Zerewitinoff active H atom. The Zerewitinoff active H atom indicates an acidic H atom or "active" H atom within the scope of the present invention. It can be conventionally determined through a reaction with an appropriate Grignard reagent. The quantity of Zerewitinoff active H atoms is typically measured through the release of methane, which occurs according to a following reaction equation in a reaction of the substance to be tested with methylmagnesium bromide (CH3-MgBr):

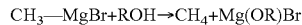

$CH_3—MgBr+ROH \rightarrow CH_4+Mg(OR)Br$

Zerewitinoff active H atoms typically originate from C—H acidic, organic groups, —OH, —SH, —NH2 or —NHR with R as an organic radical, and —COOH.

Particularly suitable H functional starter compounds have one H functionality of 1 to 35, particularly 1 to 16, preferably 1 to 8, wherein the H functionality relates to the aforementioned Zerewitinoff active H atoms.

Polyhydroxy functional polymers, which are especially selected from straight-chain and/or branched polyethers, polyesters, polyether-polyesters, polycarbonates, polyether-polycarbonates and combinations thereof, are particularly suitable as H functional starter compounds.

Insofar as the polymer bearing hydroxyl groups used as an H functional starter compound is a polyether or has polyether groups, they contain more preferably ethylene oxide units, wherein the proportional weight of ethylene oxide units in such a prefinished alkylene oxide addition product is particularly at least 40% by weight, preferably at least 50% by weight. For example, the proportional weight of ethylene oxide units is 40 to 90% by weight, preferably 50 to 80% by weight, respectively related to the mass of the polymer bearing hydroxyl groups. The radical of the polyether structure or polyether components can respectively be formed through other alkylene oxide units, in particular, e.g. (poly)propylene oxide, (poly)butylene oxide or other (poly)alkylene oxides groups and mixtures. The molecular weights of the H functional starter compounds may vary broadly. Thus, the average molar weight may be, for example, 17 to 10000 g/mol, particularly more than 200 to 9000 g/mol. The average molar weight designates the number average of polymeric compounds, which can be determined using conventional methods, e.g. via gel permeation chromatography or determining the OH value. In other words, a monomeric starter compound can be chosen as an H functional starter compound for the prepolymer pursuant to the invention, such as ammonia or ethylene glycol. Oligomeric starter compounds are also included, for example, polyethers with an average molar weight of 200 to 600 g/mol as well as polymeric starter compounds with high molecular weights, e.g. of more than 600 to 10000 g/mol or 800 to 9000 g/mol.

In addition to hydroxy-functional starters, which are to be preferably used, amino functional starters may also be used. Examples for hydroxy-functional starter compounds are methanol, ethanol, 1-propanol, 2-propanol and higher aliphatic monols, particularly fatty alcohols, phenol, alkyl-substituted phenols, propylene glycol, ethylene glycol, diethylene glycol, dipropylene glycol, 1,2-butanediol, 1,3-butanediol, 1,4-butanediol, hexanediol, pentanediol, 3-methyl-1,5-pentanediol, 1,12-dodecanediol, glycerin, trimethylolpropane, pentaerythritol, sorbitol, sucrose, hydroquinone, brenzcatechol, resorcinol, bisphenol F, bisphenol A, 1,3,5-trihydroxybenzene, as well as condensates containing methylol groups consisting of formaldehyde and phenol or urea. Highly functional starter compounds may also be used based on hydrogenated starch hydrolysis products. These are described, for example, in EP 1525244 A1.

Examples for H functional starter compounds containing amino groups are ammonia, ethanolamine, diethanolamine, triethanolamine, isopropanolamine, diisopropanolamine, ethylenediamine, hexamethylenediamine, aniline, the isomers of toluidine the isomers of diaminotoluene, the isomers of diaminodiphenylmethane as well as more solid products being made with the condensation of aniline with formaldehyde to diaminodiphenylmethane, in addition to condensates comprised of formaldehyde and melamine containing methylol groups, as well as Mannich bases. Additionally, ring-opening products from cyclical carboxylic acid can also be used as starter compounds in hydrides and polyols. Examples are ring-opening products comprised of phthalic acid anhydride or succinic acid anhydride on the one hand, and ethylene glycol, diethylene glycol, 1,2-butanediol, 1,3-butanediol, 1,4-butanediol, hexanediol, pentanediol, 3_me_thyl-1,5-pentanediol, 1,12-dodecanediol, glycerin, trimethylolpropane, pentaerythritol or sorbitol on the other. In addition, it is also possible to used single or multi-functional carboxylic acid directly as starter compounds.

Furthermore, prefabricated alkylene oxide addition productions of said starter compounds, i.e. polyether polyols preferably with OH values of 5 to 1000 mg KOH/g, preferably 10 to 1000 mg KOH/g, can also be used in the process as starter compounds or added to the reaction mixture. It is also possible to use polyester polyols as co-starters preferably with OH values in the range of 6 to 800 mg KOH/g in the process pursuant to the invention. In this regard, suitable polyester polyols can be produced according to conventional methods, for example, from organic dicarboxylic acids with 2 to 12 carbon atoms and multivalent alcohols, preferably diols with 2 to 12 carbon atoms, preferably 2 to 6 carbon atoms.

Moreover, as H functional starter substances, polycarbonate polyols, polyester carbonate polyols or polyether carbonate polyols, preferably polycarbonate diols, polyester carbonate diols or polyether carbonate diols, preferably respectively having OH values in the range of 6 to 800 mg KOH/g, can be used as starters or co-starters. These are produced, for example, through a reaction of phosgene, dimethyl carbonate, diethyl carbonate or diphenyl carbonate with di or higher functional alcohols or polyester polyols or polyether polyols.

Polyether carbonate polyols can also be used as they are achieved, e.g. through a catalytic reaction of alkylene oxides (epoxides) and carbon dioxide in the presence of H functional starter substances (see, e.g. EP-A 2046861). These polyether carbonate polyols preferably have an OH value of $\geq 5$ mg KOH/g to $\leq 240$ mg KOH/g, particularly preferably $\geq 9$ to $\leq 200$ mg KOH/g.

In step a) of the production of the prepolymer pursuant to the invention, preferably amino group-free H functional starter compounds with hydroxyl groups serve as carriers of active hydrogen, such as methanol, ethanol, 1-propanol, 2-propanol and higher aliphatic monols, particularly fatty alcohols, phenol, alkyl-substituted phenols, propylene glycol, ethylene glycol, diethylene glycol, dipropylene glycol, 1,2-butanediol, 1,3-butanediol, 1,4-butanediol, hexanediol, pentanediol, 3-methyl-1,5-pentanediol, 1,12-dodecanediol, glycerin, trimethylolpropane, pentaerythritol, sorbitol, sucrose, hydroquinone, brenzcatechol, resorcinol, bisphenol F, bisphenol A, 1,3,5-trihydroxybenzol, condensates of formaldehyde and phenol containing methylol groups, and hydrated starch hydrolysis products. Mixtures of H functional starter compounds can be used as well.

As alkylene oxide compounds usable pursuant to the invention, those substitutes may by selected that have 2 to 24 carbon atoms, particularly 2 to 12 carbon atoms, more preferably 2 to 6 carbon atoms, as well as the combination of various alkylene oxide compounds of the aforementioned type. Epoxides having 2 to 24 carbon atoms are, e.g. one or more compounds selected from the group comprised of ethylene oxide, propylene oxide, 1-butene oxide, 2,3-butene oxide, 2-methyl-1,2-propene oxide (isobutene oxide), 1-pentene oxide, 2,3-pentene oxide, 2-methyl-1,2-butene oxide, 3-Methyl-1,2-butenoxide, 1-hexene oxide, 2,3-hexene oxide, 3,4-hexene oxide, 2-methyl-1,2-pentene oxide, 4-methyl-1,2-pentene oxide, 2-ethyl-1,2-butene oxide, 1-heptene oxide, 1-octene oxide, 1-nonene oxide, 1-decene oxide, 1-undecene oxide, 1-dodecene oxide, 4-methyl-1,2-pentene oxide, butadiene monoxide, isoprene monoxide, cyclopentene oxide, cyclohexene oxide, cycloheptene oxide, cyclooctene oxide, styrene oxide, methylstyrene oxide, pinene oxide, one or more epoxidized fats as mono, di, and triglycerides, epoxidized fatty acids, C1-C24 esters of epoxidized fatty acids, epichlorohydrin, glycidol, and derivatives of glycidol, such as methyl glycidyl ether, ethyl glycidyl ether, 2-Ethyl hexyl glycidyl ether, allyl glycidyl ether, glycidyl methacrylate as well as epoxide functional alkyloxy silanes, such as 3-glycidyloxypropyl trimethoxysilane, 3-glycidyloxypropyl triethoxysilane, 3-glycidyloxypropyl tripropoxysilane, 3-glycidyloxypropyl methyldimethoxysilane, 3-glycidyloxypropyl ethyldiethoxysilane, and 3-glycidyloxypropyl triisopropoxysilane. Ethylene oxide and/or propylene oxide are preferably used. In particular, the proportional weight of ethylene oxide related to the overall mass of the dispensed alkylene oxide compounds is at least 40% by weight, preferably at least 50% by weight. For example, the proportional weight of ethylene oxide is 40 to 90% by weight, preferably 50 to 80% by weight respectively related to the overall mass of the dispensed alkylene oxide compounds.

The invention provides that the isocyanate prepolymer contains components stemming from lactides, glycolides, and/or cyclical dicarboxylic acid anhydrides, which are integrated in the polymer chain of the preliminary stage bearing hydroxyl groups through a statistic copolymerization. In a preferred manner, the molar ratio of alkylene oxide compound to this comonomer in the preliminary stage bearing hydroxyl groups is 200:1 bis 1:1, particularly 10:1 to 5:1. These molar ratios are particularly preferable because a tissue adhesive containing such a prepolymer preliminary stage has a good adhesive capacity with a minimal hardening time and it also degrades rapidly under physiological conditions.

Principally, it is also possible to integrate additional comonomers, such as cyclical anhydrides or carbon dioxide, into the polymer chain of the prepolymer bearing hydroxyl groups through statistic copolymerization.

In a preferable manner, it is possible that the polyfunctional isocyanate used in step b) is selected from aliphatic isocyanates, particularly from hexamethylene diisocyanate (HDI), isophorone diisocyanate (IPDI), butylene diisocyanate (BDI), bisisocyanatocyclohexylmethane (HMDI), 2,2,4-Trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate, diisocyanatododecane or combinations thereof. In this regard, hexamethylene diisocyanate (HDI), isophorone diisocyanate (IPDI), butylene diisocyanate (BDI), and bis(isocyanatocyclohexyl)methane (HMDI) are preferable. Particularly preferable are hexamethylene diisocyanate, isophorone diisocyanate, butylene diisocyanate, very particularly preferably hexamethylene diisocyanate and isophorone diisocyanate.

However, the invention is principally not limited to the use of aliphatic isocyanates, thus conventional aromatic isocyanates can be used, such as toluoleic diisocyanate (TDI) or diphenylmethane diisocyanate (MDI).

The reaction of the prepolymer bearing hydroxyl groups obtained according to step a) with the polyfunctional isocyanate in step b) can occur with an NCO/OH ratio of 4:1 to 12:1, preferably 8:1, and subsequently, the share of unreacted isocyanate can be divided using suitable methods. Normally, thin film distillation is used for this, wherein a prepolymer is obtained with a residual monomer content of less than 1% by weight, preferably less than 0.1% by weight, very particularly preferably less than 0.03% by weight.

Stabilizers, such as benzoyl chloride, isophthaloyl chloride, dibutyl phosphate, 3-chlorpropione acid or methyl tosylate can potentially be added during the production of the isocyanate functional prepolymer.

The reaction temperature for the reaction in step b) is preferably 20 to 120° C. and more preferably 60 to 100° C.

The isocyanate functional prepolymer preferably has an average NCO content of 2 to 10% by weight, preferably 2.5 to 8% by weight measured according to DIN EN ISO 11909.

The average NCO functionality of the isocyanate functional prepolymer is preferably 1.5 to 6, more preferably 1.6 to 5, even more preferably 1.7 to 4, and very particularly preferably 1.8 to 3.5, and particularly 3.

A further object of the present invention relates to a process for producing an isocyanate functional prepolymer comprising the steps:

a) a reaction of an H functional starter compound having at least one Zerewitinoff active H atom with an alkylene oxide and a comonomer to a preliminary stage bearing hydroxyl groups, wherein said comonomer is selected from the group comprising lactides, glycolides, cyclical dicarboxylic acid anhydrides as well as combinations thereof and wherein said comonomer is integrated through statistical copolymerization into the polymer chain(s) of a preliminary stage bearing hydroxyl groups, and b) a reaction of the preliminary stage bearing hydroxyl groups from step a) with a polyfunctional isocyanate to an isocyanate functional prepolymer.

The process pursuant to the invention can be completed without uncatalyzed, wherein however the use of a catalyst is preferable. In this regard, particularly step a) can be catalyzed using a double metal cyanide catalyst (DMC catalyst), which contains in particular zinc hexacyanocobaltate (III), zinc hexacyanoiridate (III), zinc hexacyanoferrate (III) or cobalt(II) hexacyanocobaltate (III).

A particular benefit of this configuration of the process pursuant to the invention lies in the fact that the preliminary stage bearing hydroxyl groups obtained as an intermediate product of step a) has a comparably close molecular chain length distribution. One the reasons can be seen in the use of the DMC catalyst, for such catalysts demonstrate a so-called "catch up" kinetic. This means that the catalytic activity for bonding the next monomer component successively reduces with an increased chain length, and thus the reaction speed as well.

This effect can also be used to semi-continuously or fully continuously operate the process pursuant to the invention. In the case of the semi-continuous method, a certain amount of a preliminary stage bearing hydroxyl groups is presented as a solvent, wherein this preliminary stage bearing hydroxyl groups originated from a previous production run from step a) of the process pursuant to the invention or may even have originated from other sources. The DMC catalyst ensures that the preliminary stage bearing hydroxyl groups to be newly synthesized is structured to such an extent until it reaches the approximate chain length of the preliminary stage bearing hydroxyl groups from earlier production used as a "solvent". A certain product share of the preliminary stage bearing hydroxyl groups can then be removed from the reaction mixture, e.g. 90% in order to conduct step b), wherein the remaining 10% stays for the new reaction run of step a).

Suitable DMC catalysts are generally known from the state of the art and are, for example, published in U.S. Pat. No. 3,404,109 A1, U.S. Pat. No. 3,829,505 A1, U.S. Pat. No. 3,941,849 A1, and U.S. Pat. No. 5,158,922 A1.

DMC catalyst described in U.S. Pat. No. 5,470,813 A1, EP 700949 A1, EP 743 093 A1, EP 761 708 A1, WO 97/40086 A1, WO 98/16310 A1, and WO 00/47649 A1 have a very high activity in the polymerization of alkylene oxides and enable the production of polyether polyols at very low catalyst concentrations (25 ppm or less), such that a division of the catalyst from the finished product is generally no longer necessary. A typical example is the highly active DMC catalysts described in EP 700 949 A1, which contain an additional polyether with a number average molecular weight greater than 500 g/mol in addition to a double metal cyanide compound, such as zinc hexacyanocobaltate(III) and an organic complex ligand, such as tert-Butanol. It is also possible to use the alkaline DMC catalysts published in EP application number 10163170.3.

Cyanide-free metallic salts suitable for the production of double metal cyanide compounds preferably have a general formula (II), $$M(X)_n \quad (1)$$

wherein
M is selected from the metal cations $Zn^{2+}$, $Fe^{2+}$, $Ni^{2+}$, $Mn^{2+}$, $Co^{2+}$, $Sr^{2+}$, $Sn^{2+}$, $Pb^{2+}$, and $Cu^{2+}$, M $Zn^{2+}$, $Fe^{2+}$, $Co^{2+}$ or $Ni^{2+}$ is preferred,
X represents one or more (i.e. various) anions, which is preferably selected from the group of halogenides (i.e. fluoride, chloride, bromide, iodide), hydroxide, sulfate, carbonate, cyanate, thiocyanate, isocyanate, isothiocyanate, carboxylate, oxalate, and nitrate;
n is 1 if X=sulfate, carbonate or oxalate, and
n is 2 if X=halogenide, hydroxide, cyanate, thiocyanate, isocyanate, isothiocyanate or nitrate.

Additional suitable cyanide-free metallic salts have a general formula (III), $$M_r(X)_3 \quad (III)$$

wherein
M is selected from the metal cations $Fe^{3+}$, $Al^{3+}$, and $Cr^{3+}$,
X represents one or various types of anions, wherein the anion is preferably selected from the group of halogenides (i.e. fluoride, chloride, bromide, iodide), hydroxide, sulfate, carbonate, cyanate, thiocyanate, isocyanate, isothiocyanate, carboxylate, oxalate, and nitrate;
r is 2 if X=sulfate, carbonate or oxalate, and
r is 1 if X=halogenide, hydroxide, cyanate, thiocyanate, isocyanate, isothiocyanate, carboxylate or nitrate.

Other suitable cyanide-free metallic salts have a general formula (IV), $$M(X)_s \quad (IV)$$

wherein
M is selected from the metal cations $Mo^{4+}$, $V^{4+}$, and $W^{4+}$
X represents one or various types of anions, wherein the anion is preferably selected from the group of halogenides (i.e. fluoride, chloride, bromide, iodide), hydroxide, sulfate, carbonate, cyanate, thiocyanate, isocyanate, isothiocyanate, carboxylate, oxalate, and nitrate;
s is 2 if X=sulfate, carbonate or oxalate, and
s is 4 if X=halogenide, hydroxide, cyanate, thiocyanate, isocyanate, isothiocyanate, carboxylate or nitrate.

Likewise suitable cyanide-free metallic salts have a general formula (V), $$M(X)_t \quad (V)$$

wherein
M is selected from the metal cations $Mo^{6+}$ and $W^{6+}$
X represents one or various types of anions, wherein the anion is preferably selected from the group of halogenides (i.e. fluoride, chloride, bromide, iodide), hydroxide, sulfate, carbonate, cyanate, thiocyanate, isocyanate, isothiocyanate, carboxylate, oxalate, and nitrate;
t is 3 if X=sulfate, carbonate or oxalate, and
t is 6 if X=halogenide, hydroxide, cyanate, thiocyanate, isocyanate, isothiocyanate, carboxylate or nitrate, Examples of suitable cyanide-free metallic salts are zinc chloride, zinc bromide, zinc iodide, zinc acetate, zinc acetylacetonate, iron(II)sulfate, iron(II)bromide, iron(II)chloride, cobalt(II)chloride, cobalt(II)thiocyanate, nickel(II)chloride, and nickel_(II)nitrate. Mixtures of various metallic salts may be used as well.

Metal cyanide salts suitable for the production of double metal cyanide compounds preferably have a general formula (VI)

$$(Y)_a M'(CN)_b (A)_c \quad (VI)$$

wherein

M' is selected from one or more metal cations of the group comprised of Fe(II), Fe(III), Co(II), Co(III), Cr(II), Cr(III), Mn(II), Mn(III), Ir(III), Ni(II), Rh(III), Ru(II), V(IV), and V(V), M' is preferably one or more metal cations of the group comprised of Co(I), Co(III), Fe(II), Fe(HI), Cr(III), Ir(III), and Ni(II), Y is selected from one or more metal cations of the group comprised of alkaline metal (i.e. $Li^+$, $Na^+$, $K^+$, $Rb^+$, $Cs^+$), and alkaline earth metal (i.e. $Be^{2+}$, $Ca^{2+}$, $Mg^{2+}$, $Sr^{2+}$, $Ba^{2+}$), A is selected from one or more anions of the group comprised of halogenides (i.e. fluoride, chloride, bromide, iodide), hydroxide, sulfate, carbonate, cyanate, thiocyanate, isocyanate, isothiocyanate, carboxylate, oxalate or nitrate, and a, b, and c are whole numbers, wherein the values for a, b, and co are selected in such a way that there is electroneutrality of the metal cyanide salt; a is preferably 1, 2, 3 or 4; b is preferably 4, 5 or 6; c preferably has the value of 0.

Examples of suitable metal cyanide salts are potassium hexacyanocobaltate(III), potassium hexacyanoferrate(II), potassium hexacyanoferrate(III), calcium hexacyanocobaltate(III), and lithium hexacyanocobaltate(III).

Preferred double metal cyanide compounds, which are contained in DMC catalysts pursuant to the invention, are compounds of a general formula (VII)

$$Mx[M'x'(CN)y]z \qquad (VII),$$

wherein M is defined as in formula (I) to (IV) and

M' is defined as in formula (V), and x, x', y, and z are whole numbers and selected in such a manner that there is electroneutrality of the double metal cyanide compound.

Preferably x=3, x'=1, y=6, and z=2,

M=Zn(II), Fe(II), Co(II) or Ni(II) and

M'=Co(III), Fe(III), Cr(III) or Ir(III).

Examples of preferably used double metal cyanide compounds are zinc hexacyanocobaltate(III), zinc hexacyanoiridate(III), zinc hexacyanoferrate(III), and cobalt(II)hexacyanocobaltate(III). Additional examples of suitable double metal cyanide compounds can be found, e.g. U.S. Pat. No. 5,158,922 A1. Zinc hexacyanocobaltate(III) is particularly preferably used.

The organic complex ligands added to during the production of DMC catalysts are published, for example, in U.S. Pat. No. 5,158,922 A1, U.S. Pat. No. 3,404,109 A1, U.S. Pat. No. 3,829,505 A1, U.S. Pat. No. 3,941,849 A1, EP 700949 A1, EP 761708 A1, JP 4145123 A1, U.S. Pat. No. 5,470,813 A1, EP 743 093 A1, and WO 97/40086 A1. Water-soluble organic compounds with heteroatoms, such as oxygen, nitrogen, phosphorus or sulfur, which can form complexes with the double metal cyanide compound, are, for instance, used as organic complex ligands. Preferred organic complex ligands are alcohols, aldehydes, ketones, ethers, esters, amides, urea, nitriles, sulfides, and their mixtures. Particularly preferred organic complex ligands are aliphatic ethers (such as dimethoxyethane), water soluble aliphatic alcohols (such as ethanol, isopropanol, n-butanol, iso-butanol, sec-butanol, tert-butanol, 2-methyl-3-buten-2-ol, and 2-methyl-3-butin-2-ol), compounds, which contain aliphatic or cycloaliphatic ether groups as well as aliphatic hydroxyl groups (such as ethylene glycol-mono-tert-butyl ether, diethylene glycol-mono-tert-butyl ether, tripropylene glycol-mono-methyl ether, and 3-methyl-3-oxetane-methanol). Highly preferred organic complex ligands are selected from one or more compounds of the group comprised of dimethoxyethane, tert-Butanol, 2-methyl-3-buten-2-ol, 2-methyl-3-butin-2-ol, ethylene glycol-mono-tert-butyl ether, and 3-Methyl-3-oxetane-methanol.

One or more complex-forming component(s) from the compound classes of polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylic acid-co-maleic acid), polyacrylonitrile, poly alkyl acrylates, poly alkyl methacrylates, polyvinyl methyl ethers, polyvinyl ethyl ethers, polyvinyl acetate, polyvinyl alcohol, poly-N-vinylpyrrolidone, poly(N-vinylpyrrolidone-co-acrylic acid), poly vinyl methyl ketone, poly(4-vinylphenol), poly(acrylic acid costyrene), oxazoline polymers, polyalkylene imines, maleic acid and maleic acid anhydride copolymers, hydroxyethyl cellulose and polyacetylene or of glycidyl ethers, glycosides, carboxylic acid esters of polyvalent alcohols, bile acids or their salts, esters or amides, cyclodextrins, phosphorus compounds, $\alpha,\beta$-unsaturated carboxylic acid esters or ionic surface or interfacial-active compounds are optionally used for the production of DMC catalysts preferred pursuant to the invention.

Preferably, the aqueous solutions of metallic salt (e.g. zinc chloride) used for producing the DMC catalysts pursuant to the invention in the first step in stoichiometric surplus (at least 50 mol %) in relation to metal cyanide salt, (i.e. at least one molar ratio of cyanide-free metallic salt to metal cyanide salt of 2.25 to 1.00) and the metal cyanide salt (e.g. potassium hexacyanocobaltate) in the presence of the organic complex ligands (e.g. tert-butanol) are reacted, such that a suspension forms containing the double metal cyanide compound (e.g. zinc hexacyanocobaltate), water, surplus cyanide-free metallic salt, and the organic complex ligands.

In the process, the organic complex ligand may present in the aqueous solution of the cyanide-free metallic salt and/or the metal cyanide salt or it is directly added to the suspension obtained after precipitation of the double metal cyanide compound. It has been proven to be beneficial to mix the aqueous solution of the cyanide-free metallic salt and the metal cyanide salt and the organic complex ligand while stirring vigorously. The suspension formed in the first step is then optionally treated with an additional complex forming component. In this process, the complex forming component is preferably used in a mixture with water and organic complex ligands. A preferred method for conducting the first step (i.e. production of the suspension) occurs through the use of a mixing nozzle, particularly preferably through the use of a spray dispersant, as described in WO 01/39883 A1.

In the second step, the solid matter is isolated (i.e. the preliminary stage of the catalyst pursuant to the invention) from the suspension through convention techniques, such as centrifugation or filtration.

In a preferred embodiment type for producing the catalyst, the isolated solid matter is subsequently washed in a third step of the process with an aqueous solution of the organic complex ligand (e.g. by means of re-suspension and subsequent re-isolation through filtration and centrifugation). In this manner, for example, water-soluble byproducts, such as potassium chloride, can be removed from the catalyst pursuant to the invention. The quantity of organic complex ligand in the aqueous washing solution is preferably between 40 and 80% by weight in relation to the overall solution.

In the third step of the aqueous washing solution, an additional complex-forming component, preferably in the range between 0.5 and 5% by weight in relation to the overall solution, is optionally added.

Furthermore, it is beneficial to wash the isolated solid matter more than once. In this regard, e.g. the first washing process can be repeated. However, it is preferable to not use aqueous solutions for additional washing processes, e.g. a mixture of organic complex ligands and another complex-forming component.

The isolated and potentially washed solid matter is subsequently, potentially after pulverization, dried at temperatures of generally 20-100° C. and with pressures of generally 0.1 mbar to normal pressure (1013 mbar).

A preferred method for isolating DMC catalysts pursuant to the invention from the suspension through filtration, filter cake washing, and drying is described in WO 01/80994 A1.

The concentration of the DMC catalyst used in step a) is 5 to 1000 ppm, preferably 10 to 900 ppm, and particularly preferably 20 to 500 ppm in relation to the amount of the prepolymer bearing hydroxyl groups to be produced. Depending on the requirement profile of the application, the DMC catalyst can be left if the product or (partially) separated. The DMC catalyst can be (partially) separated, for example, by treating with adsorbents. Processes for the separation of DMC catalysts are described, for example, in U.S. Pat. No. 4,987,271 A1, DE 313 22 58 A1, EP 406 440 A1, U.S. Pat. No. 5,391,722 A1, U.S. Pat. No. 5,099,075 A1, U.S. Pat. No. 4,721,818 A1, U.S. Pat. No. 4,877,906 A1, and EP 385 619 A1.

If the process pursuant to the invention is performed using double metal cyanide catalysts, it is still beneficial to first present the H functional starter compound, the catalyst, and the comonomer and then to dispense the alkylene oxide compound. This method has a beneficial impact on the statistic distribution of comonomer components in the polymer chain and thus improves the biological degradability of the tissue adhesive system.

In the following, step a) of the process pursuant to the invention is described in detail, wherein the present invention is not limited to the following depiction:

In one embodiment of the process pursuant to the invention, the H functional compound is initially presented with the DMC catalyst and the comonomer in a reactor/reactor system. In this regard, the entire amount of comonomer can already be presented at the beginning. Minimal amounts of an inorganic mineral acid, preferably phosphoric acid, can potentially be added to the H functional compound prior to bringing it into contact with the DMC catalyst in order to neutralize any traces of alkali in the H functional starter compound or to design the production process in a generally more stable manner.

Alternatively, it is possible to only present the H functional compound with the DMC catalyst at this point and then to continuously add the comonomer as well as the alkylene oxide, particularly parallel.

Pursuant to an additional process variation, the H functional compound and the DMC catalyst are presented first and then a partial amount of the alkylene oxide is dispensed. Thus, a chain length of the H functional compound can initially be enlarged through the formation of oxyalkylene units, which is of particular value in low-molecular H functional compounds, such as in those with an average molar weight of up to 600 g/mol. There are still no components of the comonomer present in this section. Subsequently, the comonomer as well as others or the remaining alkylene oxide can be added in order to conduct the copolymerization. In this regard, the entire amount of comonomer can be added first and then the remaining alkylene oxide can be introduced. It is also possible to continuously add the comonomer as well as the remaining alkylene oxide simultaneously.

In addition, other mixture forms are conceivable between the aforementioned process variations.

After introducing these basic variations, the details of the conducting the process should be explained in more depth. After heating to temperatures of 50 to 160° C., particularly 60 to 140° C., very particularly preferably 70 to 140° C., the content of the reactor is stripped in a preferred process variation with inert gas over a period of preferably 10 to 60 minutes while stirring. Upon stripping with inert gas, the volatile components are removed by introducing inert gases into the liquid phase with a simultaneously applied vacuum with an absolute pressure of 5 to 500 mbar. After adding typically 5 to 20% by weight of one or more alkylene oxides in relation to the amount of the presented H functional compound, and potentially of comonomers, the DMC catalyst is activated.

The addition of one or more alkylene oxides may occur prior to, during or after heating the contents of the reactor to temperatures of 50 to 160° C., preferably 60 to 140° C., very particularly preferably 70 to 140° C.; it occurs preferably after stripping. The activation of the catalyst becomes noticeable through an accelerated decrease of reactor pressure, through which the initial alkylene oxide volume/volume of the comonomer is shown.

The desired amount of alkylene oxide or alkylene oxide mixture, and potentially an additional comonomer, can then be continuously added to the reaction mixture, wherein a reaction temperature of 20 bis 200° C., preferably from 50 to 160° C. is selected. The reaction temperature is identical to the activation temperature in many cases.

The catalyst is frequently activated so quickly that dispensing a separate amount of alkylene oxide/the comonomer for the activation of the catalyst can be omitted and continuous dispensing of the alkylene oxide and, potentially the comonomer, can be directly initiated, potentially with a reduced dispense rate at first. The reaction temperature during the alkylene oxide dispensing stage/while the unsaturated, cyclical carboxylic acid anhydride is being dispensed may vary within the described limits. Likewise, the alkylene oxides and the comonomer may be added to the reactor differently: It is possible to dispense during the gas stage or directly in the liquid stage, e.g. via an immersion tube or a distributor ring located near the bottom of the reactor in a well-mixed area.

In the case of DMC catalyst processes, dispensing during the liquid stage is preferred. The alkylene oxide and the comonomer should be continuously added to the reactor in such a way that the safety-related pressure limits of the reactor system being used are not exceeded. It is necessary to ensure that sufficient inert gas partial pressure is maintained in the reactor during the start-up and dispensing stage, particularly when codispensing alkylene oxide mixtures containing ethylene oxide or pure ethylene oxide. This can be configured, e.g. through noble gas or nitrogen.

When dispensing during the liquid stage, the dispensing units should be designed to self-empty, for example, by making dispensing holes on the bottom of the distributor ring. A backflow of reaction medium into the dispensing units and reactant templates should generally be prevented through technical measures on the machine. If an alkylene oxide/comonomer mixture is dispensed, the respective alkylene oxides and respective comonomers can be added to the reactor separately or as a mixture. A preliminary mixture of alkylene oxides among each other and with the comonomer can be achieved, for example, through a mixing unit ("inline blending") located in the common dispensing section.

Dispensing alkylene oxides and potentially the comonomer on the pump discharge side, for example, via pump circulation controlled by heat exchangers, separately or premixed has also been proven positive. For proper mixing with the reaction medium, it is beneficial to integrate a high-shear mixing unit into the alkylene oxide/comonomer/reaction medium flow. The temperature of an exothermic ring-opening addition reaction is maintained at the desired level through cooling. According to the state of the art regarding the design of polymerization reactors for exothermic reactions (e.g. Ullmann's Encyclopedia of Industrial Chemistry, Vol. B4, pp. 167ff, 5th Ed., 1992), this cooling occurs in general via a reactor wall (e.g. double shell, half-coil pipe) as well as via additional heat exchanger areas situated inside the reactor and/or externally in the pump circulation, e.g. to cooling coils, cooling plugs, panel tube bundle or mixer heat exchangers. They should be configured such that they can provide effective cooling already at the beginning of the dispensing stage, i.e. when filled minimally.

Generally, it is necessary to ensure proper mixing of the reactor contents in all reaction stages through the configuration and use of commercial agitators, wherein particularly single or multi-stage arranged agitators or agitator types operating extensively across the fill level are suitable in this case (see, e.g. the "Apparatuses" manual; Vulkan-Verlag Essen, 1st Edition (1990), pp. 188-208). Particularly technically relevant in this case is a mixing energy introduced in the medium throughout the content of the reactor, which is generally in the range of 0.2 to 5 W/l, with respectively higher local performance levels in the area of the agitator itself and potentially at low fill levels. To achieve optimal agitation, combination of baffles (e.g. flat or tubular baffles) and cooling coils (or cooling plugs) can be arranged in the reactor pursuant to the state of the art, which can extend across the floor of the container. The agitation capacity of the mixing unit may also vary during the dispensing stage depending on the fill level to ensure a particularly high energy input in critical reaction stages. For example, it can be beneficial to mix dispersions containing solid matter, which may be present at the beginning of a reaction, e.g. when using sucrose, particularly intensively.

Additionally, it is necessary to ensure that sufficient dispersion of solid matter in the reaction mixture is guaranteed through the selection of the agitation unit, particularly when using solid H functional starter compounds. In this case, agitation stages on the floor of the reactor as well as agitators suitable in particular for suspending are preferably used. Furthermore, the shape of the agitators should help reduce the foaming of reaction products. The foaming of reaction mixtures can be observed, for example, at the end of the dispensing and subsequent reaction stage if residual epoxides are additionally removed in the vacuum at absolute pressures in the range of 1 to 500 mbar. Agitators that achieve continuous mixing of the liquid surface have proven to be suitable for such cases. Depending on the requirement, the agitator shaft has a floor support and potentially additional support bearings in the container. In this regard, the agitator shaft can be driven from above or from below (with the shaft arranged centrically or eccentrically).

Alternatively, it is also possible to achieve necessary mixing exclusively by means of pump circulation controlled by a heat exchanger or to operate it as an additional mixing component aside from the agitator unit, wherein the reaction content is transferred as needed (typically 1 to 50 times per hour).

Various reactor types are suitable for conducting the process pursuant to the invention. Cylindrical containers having a height to diameter ratio of 1:1 to 10:1 are preferably used. Spherical, torispherical, flat or conical floors can be considered, for example, as reactor floors.

Following completion of the dispensing of alkylene oxide and the comonomers in step a), a subsequent reaction stage may follow, in which residual alkylene oxide and comonomer is reacted off. The subsequent reaction stage is completed if a decrease in pressure in the reaction tank can no longer be determined. Traces of unreacted alkylene oxides and unreacted comonomer can quantitatively be removed after the reaction stage potentially in a vacuum at an absolute pressure of 1 to 500 mbar or through stripping. Stripping removes volatile components, such as (residual) alkylene oxides by introducing inert gas or water vapor in the liquid stage with a simultaneously applied vacuum (for example, by transmitting inert gas at an absolute pressure of 5 to 500 mbar). Removing volatile components, such as unreacted epoxides, can occur in a vacuum or through stripping at temperatures of 20 to 200° C., preferably 50 to 160° C. and preferably while stirring. These stripping processes may also be conducted in so-called stripping columns, in which a flow of inert gas or water vapor is transferred in the opposite direction. Stripping is preferably done with inert gas in the presence of water vapor. After achieving a consistent pressure or after removing volatile components through vacuuming and/or stripping, the product can be released from the reactor.

If the entire amount of comonomers is not presented at the beginning, the comonomer can be dispensed in step a) with process variation A) such that the dispensing of alkylene oxide is interrupted and after a subsequent reaction stage, the dispensing of additional comonomer can be reinitiated. Naturally, this process can be repeated multiple times during a reaction sequence. It is particularly preferred that the subsequent alkylene oxide block comprises a quantity of more than 1 mol of alkylene oxide per mol of active H atoms from the H functional compounds used as starter compounds.

It is likewise possible to continuously or gradually vary the ratio of dispensing speeds of alkylene oxide and the dispensing of the comonomer in an opposing manner while simultaneously adding both of these components, in which, for example, the ratio of the dispensing flow of the comonomer to that of the alkylene oxide/alkylene oxides assumes values of 0:1 to 1:0.

One characteristic of DMC catalysts is their distinctive sensitivity to high concentrations of hydroxyl groups, which, for example, are caused by large amounts of starters, such as ethylene glycol, propylene glycol, glycerin, trimethylolpropane, sorbitol or sucrose, and polar impurities of the reaction mixture or the starter(s). The DMC catalysts may not then be transferred to the polymerization active form during the reaction initiation stage. Impurities can be, e.g. water or compounds with a high number of hydroxyl groups situated in close proximity, such as carbohydrates and carbohydrate derivatives. Substances with carbonyl groups situated in close proximity or those close to hydroxyl groups have a negative effect on the activity of catalysts.

To enable starters with high concentrations of OH groups or starters with contaminants that are perceived as catalyst toxins to still undergo DMC catalyzed alkylene oxide addition reactions, the hydroxyl group concentration should be reduced or the catalyst toxins should be rendered harmless. In this regard, prepolymers can first be produced from these starter compounds by means of a basic catalyst, which are then transferred to the desired alkylene oxide addition products of high molar masses after processing by means of DMC catalysis. Prepolymers include, for example, the aforementioned "prefinished alkylene oxide addition products" suitable as starters. The disadvantage to this approach is that such prepolymers often obtained through basic catalysis have to be processed very carefully to avoid deactivating the DMC catalyst through basic catalyst traces that were potentially introduced by the prepolymer.

This disadvantage can be overcome through the so-called process of continuous starter dispensing. In this regard, critical starter compounds are not presented in the reactor, but rather are continuously added to the reactor in addition to alkylene oxides during the reaction. Prepolymers may be presented in this process as starter medium for the reaction and small amounts of the product itself can also be used as starter medium. Thus, the necessity of first having to separately produce prepolymers suitable for further alkylene oxide additions is eliminated.

Thus, in variation B) of step a) of the process pursuant to the invention, a starter polyol and the DMC catalyst are presented in the reactor system and the H functional compound is continuously added together with the alkylene oxide and the comonomer. Alkylene oxide addition products, such as polyether polyols, polyester polyols, polyetherester polyols, polycarbonate polyols, polyester carbonate polyols, polyether carbonate polyols are respectively suitable as starter polyols in step a), for example, with OH values in the range of 3 to 1000 mg KOH/g, preferably 3 to 300 mg KOH/g, and/or a preliminary stage bearing hydroxyl groups produced separately pursuant to step a). Preferably, a preliminary stage bearing hydroxyl groups produced separately pursuant to step a) is used as a starter polyol.

In a less preferred variation of this embodiment B), it is likewise possible to continuously or gradually vary the ratio of dispensing speeds of alkylene oxide and the dispensing of the comonomer in an opposing manner while simultaneously adding both of these components, in which, for example, the ratio of the dispensing flow of the comonomer to that of the alkylene oxide/alkylene oxides assumes values of 0:1 to 1:0. This embodiment is less preferred as according to it, the preliminary stage bearing hydroxyl groups pursuant to step a) is obtained in a less consistent form.

In embodiment B) of step a), the dispensing of the H functional compound and that of the alkylene oxide as well as the comonomer is preferably simultaneously completed, or the H functional compound and a first partial amount of alkylene oxide and a first partial amount of comonomer is initially added together and subsequently the second partial amount of alkylene oxide and comonomer is added, wherein the sums of the first and second partial amount of alkylene oxide and the first and second partial amount of comonomer corresponds to the total amount of the quantity of one or more alkylene oxides or of one or more comonomers used in step a). The first partial amount is preferably 60 to 98% by weight and the second partial amount is 40 to 2% by weight of the overall amount of alkylene oxide to be dispensed in step a). The first partial amount is preferably 0 to 100% by weight and the second partial amount is 100 to 0% by weight of the overall amount of one or more unsaturated, cyclical carboxylic acid anhydrides to be dispensed in step a).

If the composition of the alkylene oxides and/or the composition/dispensing rate of one or more comonomers is modified after dispensing of the H functional compound is concluded, products with multi-block structures can also be produced pursuant to process variation B). Thus, static distribution of the comonomer units has been provided within the blocks. It is preferable with process variation B) as well that dispensing of comonomers is concluded prior to dispensing alkylene oxide, particularly preferably in such a way that this concluding alkylene oxide block comprises a quantity of more than 1 mol of alkylene oxide per mol of active H atoms from the H functional compounds used as starter compounds. After adding the reagents, a subsequent reaction stage may follow, in which the use of alkylene oxide/comonomer can be quantified by monitoring the pressure. After achieving a constant pressure, the final product may be released, potentially after attaching a vacuum or through stripping to remove non-reacted alkylene oxides, as described above.

In variation C) from step a) of the process pursuant to the invention, the preliminary stages bearing hydroxyl groups can be continuously produced. In this regard, the DMC catalyst is continuously added to the reactor or a reactor system under alkoxylation conditions in addition to alkylene oxide and the H functional compound as well as the comonomer, and the product is continuously removed from the reactor or reactor system after a preselected average retention time. In the case of process variation C), it is preferable that a reactor cascade is used as a reactor system, for which a third, continuously operated reactor is located between the secondary reactor and the actual reactor, in which exclusively one or more alkylene oxides are continuously dispensed. In a particularly preferred embodiment of process variation C), this concluding alkylene oxide block comprises a quantity of more than 1 mol of alkylene oxide per mol of active H atoms from the H functional compounds used as starter compounds.

Continuous subsequent reaction stages may follow, for example in a reactor cascade or in a tube reactor. Volatile components can be removed in a vacuum and/or through stripping, as described above.

The OH values of the preliminary stages bearing hydroxyl groups obtainable pursuant to the DMC catalyzed addition step a) preferably have values of 3 mg KOH/g to 200 mg KOH/g, particularly preferably from 10 to 60 mg KOH/g, and very particularly preferably from 20 to 50 mg KOH/g.

The OH value can be determined, e.g. titrimetrically according to regulation DIN 53240 or spectroscopically via NW.

Equivalent molar mass refers to the overall mass of the material containing active hydrogen atoms divided by the number of active hydrogen atoms. In the case of materials containing hydroxy groups, it relates to the OH value as follows:

$$\text{Equivalent molar mass} = 56100/\text{OH value [mg KOH/g]}$$

Anti-aging agents, such as antioxidants, can potentially be added to the preliminary stage bearing hydroxyl groups obtainable according to step a) of the process pursuant to the invention.

Step b) occurs with this process variation as explained above.

A further object of the present invention relates to a tissue adhesive system comprising a tissue adhesive having
a component A) in the form of a isocyanate functional prepolymer pursuant to the invention and a component B) in the form of an amino functional aspartic acid ester of a general formula (VIII)

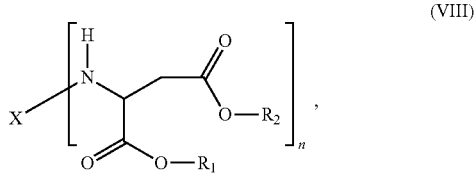

(VIII)

wherein

X is an n-value organic radical, $R_1$, $R_2$ have equal or different organic radicals having no Zerewitinoff active H atoms, n is a whole number$\geq 2$, particularly 2 or 3, and/or a reaction product of the isocyanate functional prepolymer A) with amino functional aspartic acid esters B) as component C).

Upon hardening said component A) and B), a polyurea polymer emerges, wherein said component B) functions as a hardener for said component A).

In addition to the beneficial biodegradability of the tissue adhesive systems pursuant to the invention, they are primarily distinguished by a short hardening time. The tissue adhesive systems pursuant to the invention harden at room temperature and average humidity on human skin normally within less than 5 minutes to the extent that they are no longer tacky on the surface. For example, this can be checked with a finger. Preferred tissue adhesive systems are already no longer tacky after less than 4 minutes.

Amino functional aspartic acid ester can be produced, for example, through (Michael) addition of a diester of a difunctional, unsaturated organic acid, such as diethyl maleate to the primary amino groups of an organic amine having at least two primary amino groups, such as bis(hexamethylene) triamine. For example, EP 11153810.4 highlights the production, the content of which is fully included in the present publication. In addition to diester of maleic acid, for example, diesters of tetrahydrophthalic acid, particularly those of 3,4,5,6-tetrahydrophthalic acid as well as combinations thereof, are worth consideration.

Naturally, pharmacologically active substances, such as analgesics with or without an anti-inflammatory effect, antiphlogistic, antimicrobially active substances, antimycotics, and antiparasitically active substances can be integrated in the tissue adhesive systems as well.

The active substances may be pure active substances or in the form of a capsule to achieve, for example, a time-delayed release. Within the scope of the present invention, a number of types and classes of active substances can be used as medically active substances.

One such medically active substance may comprise, for example, a component releasing nitrogen monoxide under in vivo conditions, preferably L-arginine or a component containing or releasing L-arginine, particularly preferably L-arginine hydrochloride. Proline, ornithine and/or other biogenic intermediate stages, such as biogenic polyamines (spermine, spermidine, putrescine or bioactive artificial polyamines) may be used as well. As we know, these types of components promote the healing of wounds, wherein their continuous quantitatively nearly equal release is particularly tolerable for healing wounds.

Additional active substances usable pursuant to the invention comprise at least one substance selected from the group of vitamins or provitamins, carotinoides, analgesics, antiseptics, hemostyptics, antihistamines, antimicrobial metals or their salts, substances promoting the herbal healing of wounds or substance mixtures, herbal extracts, enzymes, growth factors, enzyme inhibitors as well as combinations thereof.

Particularly non-steroid analgesics, especially salicylic acid, acetylsalicylic acid and their derivatives, e.g. Aspirin®, aniline and its derivatives, acetaminophen e.g. Paracetamol®, anthranilic acid and its derivatives, e.g. mefenamine acid, pyrazole or its derivatives, methamizole, Novalgin®, phenazone, Antipyrin®, isopropylphenazone, and very particularly preferably aryl acetic acid, as well as its derivatives, heteroaryl acetic acids and its derivatives, arylpropionic acids and its derivatives, and heteroaryl propionic acids and its derivatives, e.g. Indometacin®, Diclophenac®, Ibuprofen®, Naxoprophen®, Indomethacin®, Ketoprofen®, Piroxicam® are suitable as analgesics.

As growth factors, the following should be mentioned in particular: aFGF (Acidic Fibroplast Growth Factor), EGF (Epidermal) Growth Factor), PDGF (Platelet Derived Growth Factor), rhPDGF-BB (Becaplermin), PDECGF (Platelet Derived Endothelial Cell Growth Factor), bFGF (Basic Fibroplast Growth Factor), TGF α; (Transforming Growth Factor alpha), TGF β (Transforming Growth Factor beta), KGF (Keratinocyte Growth Factor), IGF1/IGF2 (Insulin-Like Growth Factor), and TNF (Tumor Necrosis Factor).

Particularly those fat-soluble or water soluble vitamins, vitamin A, group of retinoids, provitamin A, group of carotenoids, particularly β-carotene, vitamin E, group of tocopherols, particularly α Tocopherol, β-Tocopherol, γ-Tocopherol, δ-Tocopherol, and α-Tocotrienol, β-Tocotrienol, γ-Tocotrienol, and δ-Tocotrienol, vitamin K, phylloquinone, particularly phytomenadione or herbal vitamin K, vitamin C, L-ascorbic acid, vitamin B 1, thiamin, vitamin B2, riboflavin, vitamin G, vitamin B3, niacin, nicotinic acid, and nicotinic acid amide, vitamin B5, pantothenic acid, provitamin B5, panthenol or dexpanthenol, vitamin B6, vitamin B7, vitamin H, biotin, vitamin B9, folic acid as well as combinations thereof are suitable as vitamins or provitamins.

As an antiseptic, it is necessary to use a medium that works as a germicide, bactericide, bacteriostatic, fungicide, virucide, virustatic, and/or general microbiocide.

Particularly those substances that are selected from the group of resorcinol, iodine, iodine povidone, chlorhexidine, benzalkonium chloride, benzoic acid, benzoyl peroxide or cethylpyridiniumchloride are suitable. Moreover, particularly antimicrobial metals can be used as antiseptics. Particularly silver, copper or zinc, as well as their salts, oxides or complexes can be used together or independently as antimicrobial metals.

In conjunction with the present invention, particularly chamomile extracts, hamamelis extracts, e.g. *Hamamelis virginiana*, calendula extract, aloe extract, e.g. *aloe vera, Aloe barbadensis, Aloe ferox* or *Aloe vulgaris*, green tea extracts, seaweed extract, e.g. red algae or green algae extract, avocado extract, myrrh extract, e.g. *Commophora molmol*, bamboo extracts as well as combinations thereof are referred to as herbal active substances promoting the healing of wounds.

The content of the active substances is primarily aligned with the medically necessary dose as well as tolerability with the remaining components of the composition pursuant to the invention.

In a particularly preferable variation, it is possible to select from structures of a general formula (IX) with the tissue adhesive system of amino functional aspartic acid esters pursuant to the invention

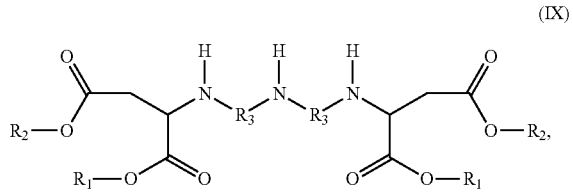

(IX)

wherein $R_1$, $R_2$, $R_3$ have equal or different organic radicals having no Zerewitinoff active H atoms, wherein $R_1$ and $R_2$ are selected in particular from methyl, ethyl, propyl, and butyl radicals, and $R_3$ is selected in particular from straight-chain or branched alkylene diradicals with 1 to 12 carbon atoms, preferably with 3 to 7 carbon atoms.

However, the tissue adhesive system pursuant to the invention is not limited solely to the use of the aforementioned hardeners (component B), but rather can also have one or more additional hardeners. Thus, the tissue adhesive system pursuant to the invention also comprises an additional hardener according to a particularly preferable embodiment, which is selected particularly from polyols having a number average molar mass of 1000 Da or less, particularly 600 Da or less, more preferably 400 Da or less or even 300 Da or less. PEG or PPG, for example, are suitable as polyols. Through the addition of these extra hardeners, the hardening speed of the tissue adhesive system pursuant to the invention can be influenced, i.e. normally shortened, such that it is possible to package the tissue adhesive on an as-needed basis.

According to an additional variation of the tissue adhesive system pursuant to the invention, it also comprises a flat protective layer, with which the tissue adhesive can be applied, wherein the protective layer is particularly metal foil, synthetic foil, fleece, tissue, cloth, fabric or a combination thereof. In this manner, the adhesive can be pressed onto the area to be adhered, such as a wound, to improve adhesion and to prevent running of the adhesive, without the user having to touch the adhesive in the process. Additionally, bleeding can be more easily stopped as due to the pressure applied during the application, the blood vessels are also compressed locally. The protective layer can then be left on the area or removed as well. In this regard, the protective layer necessarily has to be provided with an anti-adhesive coating at least on the side opposite the adhesive, such as a silicon coating on the surface of concern.

The invention also relates to a dispensing system having at least two chambers for a tissue adhesive system according to this invention, wherein said dispensing system is distinguished by the fact that said component A) is contained in one chamber and said component B) and potentially said components C) of the tissue adhesive system are contained in another.

A further object of the invention is adhesive films as well as composite parts produced as a result, which can be obtained from the tissue adhesive system pursuant to the invention.

Lastly, the object of the present invention is a process for closing or bonding cell tissue, for which the tissue adhesive system pursuant to the invention is used.

The present invention will be explained in more depth based on application examples. If otherwise specified, all percentage information relate to weight.

Methods:

The OH values were determined according to the regulation of DIN 53240.

The viscosities of the polyols were determined with rotation viscometers (Physica MCR 51, manufacturer: Anton Paar) according to the regulation of DIN 53018.

The number average $M_n$ and the weight average $M_w$ of the molecular weight as well as the polydispersity ($M_w/M_n$) were determined using gel permeation chromatography (GPC). DIN 55672-1: was used for this process: "Gel Permeation Chromatography, Part 1—Tetrahydrofuran as an Eluent" (SECurity GPC system of PSS Polymer Service, flow rate 1.0 ml/min; Columns: 2×PSS SDV linear M, 8×300 mm, 5 μm; RID detector). Polystyrene samples of known molar masses were used in the process for calibration.

NCO contents were determined volumetrically according to DIN-EN ISO 11909 if not otherwise expressly specified.

The residual monomer content was determined according to DIN ISO 17025.

Producing the Polyols

Preliminary Stage 1 Bearing Hydroxyl Groups (Polyol 1):

98.1 g of a glycerin-started poly(oxypropylene)triol with an OH value=400 mg KOH/g, 48.4 g of dilactide as well as 0.107 g of a DMC catalyst (produced according to WO 01/80994 A1, example 6 there) were presented in a 2 liter stainless steel pressure reactor under nitrogen and subsequently heated to 100° C. After 30 minutes of stripping with nitrogen at 0.1 bar, the temperature is increased to 130° C. and a mixture comprised of 701.8 g of ethylene oxide and 217.8 g of propylene oxide are then dispensed at this temperature within 130 minutes. After a subsequent reaction time of 45 minutes at 130° C., volatile shares are distilled off in a vacuum at 90° C. for 30 minutes and the reaction mixture is then cooled to room temperature.

Product Properties:

OH value: 33.7 mg KOH/g

Viscosity (25° C.): 1370 mPa

Polydispersity (Mw/Mn): 1.13

Preliminary Stage 2 Bearing Hydroxyl Groups (Polyol 2):

140.0 g of a propylene glycol-started poly(oxypropylene) diol with an OH value=260 mg KOH/g, 145.3 g of dilactide as well as 0.087 g of a DMC catalyst (produced according to WO 01/80994 A1, example 6 there) were presented in a 2 liter stainless steel pressure reactor under nitrogen and subsequently heated to 100° C. After 15 minutes of stripping with nitrogen at 0.1 bar, the temperature is increased to 130° C. and a mixture comprised of 526.8 g of ethylene oxide and 54.5 g of propylene oxide are then dispensed at this temperature within 80 minutes. After a subsequent reaction time of 75 minutes at 130° C., volatile shares are distilled off in a vacuum at 90° C. for 30 minutes and the reaction mixture is then cooled to room temperature.

Product Properties:

OH value: 29.3 mg KOH/g

Viscosity (25° C.): 1185 mPa

Polydispersity (Mw/Mn): 1.41

Producing the Isocyanate Functional Prepolymers:

Synthesis of Isocyanate Functional Prepolymers 1:

183.1 g of hexamethylene diisocyanate (HDI) and 0.9 g of benzoyl chloride were presented in a 1 l four-neck flask. 478.7 g of polyol 2 were added within 2 hours at 80° C. and subsequently stirred for 1 hour. The surplus HDI was then distilled off through thin film distillation at 130° C. and 0.13 mbar. Prepolymer 1 is obtained with an NCO content of 2.38%. The residual monomer content was <0.03% HDI.

Viscosity: 4930 mPa/23° C.

Synthesis of Isocyanate Functional Prepolymers 2:

293 g of HDI and 1.5 g of benzoyl chloride were presented in a 1 liter four-neck flask. 665.9 g of polyol 1 were added within 2 hours at 80° C. and subsequently stirred for 1 hour. The surplus HDI was then distilled off through thin film distillation at 130° C. and 0.13 mbar. Prepolymer 2 is obtained with an NCO content of 2.37%. The residual monomer content was <0.03% HDL Viscosity: 5740 mPa/23° C.

Producing the Aspartate Hardener:

Aspartate A:

1 mol of 2-Methyl-1,5-diaminopentane was slowly added to 2 mol of diethyl maleate drop-wise, such that the reaction temperature did not exceed 60° C. Subsequently, it was heated to 60° C. until no more diethyl maleate could be detected in the reaction mixture. A quantitative reaction took place.

Aspartate B:

1 mol of bis(hexamethylene)triamine was slowly added to 2 mol of diethyl maleate drop-wise, such that the reaction temperature did not exceed 60° C. Subsequently, it was heated to 60° C. until no more diethyl maleate could be detected in the reaction mixture. A quantitative reaction took place.

Producing the Tissue Adhesive:

Producing Tissue Adhesive 1:

4 g of the isocyanate functional prepolymer 2 were stirred well in a cup with an equivalent amount of aspartate A. Directly thereafter, a thin coat of reaction mixture was applied to the tissue to be bonded. Hardening to a transparent film with a respectively strong bond took place within 2 minutes. The surface of the adhesive was no longer tacky after 6 minutes. The processing time was 5 minutes 45 seconds.

Producing Tissue Adhesive 2:

4 g of the isocyanate functional prepolymer 1 were stirred well in a cup with an equivalent amount of aspartate B. Directly thereafter, a thin coat of reaction mixture was applied to the tissue to be bonded. Hardening to a transparent film with a respectively strong bond took place within 1 minute. The surface of the adhesive was no longer tacky after 3 minutes. The processing time was 1 minutes 30 seconds.

Determining the Biodegradability:

The tissue adhesive system to be tested was hardened in a tube (diameter: 0.5 cm, length 2 cm). The resulting 2.7 g heavy test sample was agitated in 10 ml of buffer solution (pH: 7.4, Aldrich: P-5368) at 60° C. or 37° C. in an agitation incubator with 150 RPM until the material was completely dissolved, i.e. without residuum.

The samples had completed degraded after the following periods:

Tissue adhesive 1: 11 weeks at 60° C.
Tissue adhesive 2: 6 weeks at 60° C.

Determining the Cytotoxicity:

The hardened tissue adhesive 2 was tested according to ISO 10993-5:2009 with L 929 cells for cytotoxicity. The material proved to be non-cytotoxic.

Acceleration of the Hardening Speed:

To increase the hardening speed of the tissue adhesive to be able to apply the system to a 4:1 double-chamber spraying system, sufficient polyethylene glycol (PEG) 200 was mixed into the hardener, aspartate A, that a mixture ratio of 4 ml of isocyanate functional prepolymer 2 and 1 ml of hardener resulted. The hardening time was shortened to 1 minute 30 seconds, which corresponded to the processing time.

To further increase the hardening speed, which is essential in the case of severe bleeding, various mixtures of PEG 200 as well as aspartates A and B were produced. The amounts were selected in such a manner in the process that the volume ratio of prepolymer to hardener remained 4:1.

| Hardener | Mixture ratio | Processing time |
|---|---|---|
| Aspartate A | / | 5 min. 45 seconds |
| Aspartate A/PEG 200 | 0.57/0.43 | 1 min. 40 seconds |
| Aspartate A/Aspartate B/PEG 200 | 0.369/0.098/0.53 | 1 min. 10 seconds |
| Aspartate A/Aspartate B/PEG 200 | 0.29/0.175/0.55 | 40 seconds |

In Vivo Tests on a Laboratory Pig with a Mixture of Isocyanate Functional Prepolymer 2 and Aspartate A/Aspartate B/PEG 200 to the Ratios: 0.29/0.175/0.55:

Treatment of a Lung Fistula:

An approx. 4 cm large piece of the lung was surgically removed, wherein there was a lung fistula. The diameter of the bronchus was approx. 3 mm. Arterial bleeding occurred as well. Approx. 3 ml of the adhesive was applied from a 4:1 double chamber syringe from the company, Medmix. The adhesive was pressed onto the wound with suitable foil to prevent running. The adhesive hardened within approx. 30 seconds. The lung was sealed up, the bleeding stopped. The adhesive withstood a ventilator pressure of 22 mmHg.

Comparison Test—Sealing a Lung Fistula with Fibrin Adhesive:

The same procedure was repeated. Instead of the described adhesive, fibrin (Tisseel) was used. The preparation time for mixing the fibrin adhesive was approx. 10 min. After applying on the fistula, a drop of blood formed instantaneously, under which, however, air still escaped. The fistula could not be sealed.

Heart Stab Wound:

The coronary artery in the left ventricle of the heart was injured with a scalpel, wherein an approx. 1 cm long wound was produced with spraying hemorrhaging. 5 ml of the adhesive was applied from a 4:1 double-chamber syringe from the company, Medmix. The adhesive was pressed onto the wound with suitable foil to prevent running. The wound was able to be completely sealed within 40 seconds and maintained a constant blood pressure of 140 mmHG.

The invention claimed is:

1. A method for closing or bonding cell tissue comprising providing a tissue adhesive system comprising a tissue adhesive comprising a component A), an isocyanate functional prepolymer obtained by reacting an H functional starter compound having at least one Zerewitinoff active H atom with an alkylene oxide and a comonomer to a preliminary stage bearing hydroxyl groups, wherein said comonomer is selected from the group consisting of lactides, glycolides, cyclical dicarboxylic acid anhydrides, and mixtures thereof and wherein said comonomer is integrated through statistical copolymerization into the polymer chain(s) of a preliminary stage bearing hydroxyl groups, and reacting the preliminary stage bearing hydroxyl groups from step a) with a polyfunctional isocyanate to an isocyanate functional prepolymer, and a component B), an amino functional aspartic acid ester of formula (II)

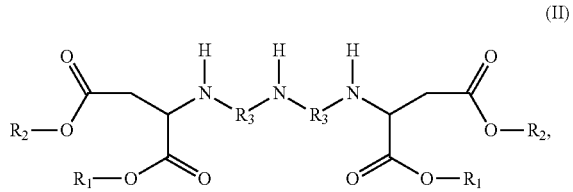

(II)

wherein $R_1$, $R_2$, $R_3$ are equal or different organic radicals having no Zerewitinoff active H atoms, and/or a reaction product of the isocyanate functional prepolymer A) with amino functional aspartic acid esters B) as component C), and applying the tissue adhesive system to the cell tissue to be bonded.

2. The method according to claim 1, wherein said H functional starter compound has 1 to 35 Zerewitinoff active H atoms.

3. The method according to claim 1, wherein said H functional starter compound has an average molar weight of 17 to 10000 g/mol.

4. The method according to claim 1, wherein an alkylene oxide compound comprises 2 to 24 carbon atoms.

5. The method according to claim 4, wherein said alkylene oxide compound is selected from ethylene oxide and/or propylene oxide, wherein the share of ethylene oxide units in a polymer chain of a preliminary stage bearing hydroxyl groups is at least 40% by weight.

6. The method according to claim 1, wherein a selected molar ratio of said alkylene oxide compound to a comonomer selected during the production of said preliminary stage bearing hydroxyl groups is 200:1 to 1:1.

7. The method according to claim 1, wherein the polyfunctional isocyanate is selected from the group consisting of aliphatic isocyanates, hexamethylene diisocyanate (HDI), isophorone diisocyanate (IPDI), butylene diisocyanate (BDI), bis-isocyanate cyclohexylmethane (HMDI), 2,2,4-Trimethylhexamethylene diisocyanate, bis-isocyanate methylcyclohexane, bis-isocyanate methyltricyclodecane, xylene diisocyanate, tetramethylxylylene diisocyanate, norbornene diisocyanate, cyclohexane diisocyanate, diisocyanate dodecane, and mixtures thereof.

8. The method according to claim 1, wherein $R_1$ and $R_2$ are identically or different, methyl, ethyl, propyl, or butyl radicals, and $R_3$ is a straight-chain or branched alkylene diradical with 1 to 12 carbon atoms.

9. The method according to claim 1, wherein said tissue adhesive system comprises an additional hardener.

10. The method according to claim 1, wherein said tissue adhesive system comprises a flat protective layer.

11. The method according to claim 1, wherein the tissue adhesive system is applied with a dispensing system comprising at least two chambers, wherein said component A) is contained in a first chamber and said component B) and optionally said components C) of the tissue adhesive system are contained in a second chamber.

12. The method according to claim 1, wherein the tissue adhesive system is non-cytotoxic.

13. The method according to claim 1, wherein the tissue adhesive system is biologically degradable.

14. The method according to claim 1, wherein the tissue adhesive system is not tacky after less than 4 minutes.

* * * * *